United States Patent
Kishimoto et al.

(10) Patent No.: US 6,281,378 B1
(45) Date of Patent: Aug. 28, 2001

(54) VANADIUM-CONTAINING CATALYSTS, PROCESS FOR MANUFACTURING AND USE OF THE SAME

(75) Inventors: Nobuji Kishimoto; Etsushige Matsunami, both of Himeji (JP)

(73) Assignee: Nippon Shokubai Co., Ltd., Osaka (JP)

(*) Notice: Subject to any disclaimer, the term of this patent is extended or adjusted under 35 U.S.C. 154(b) by 0 days.

(21) Appl. No.: 09/586,777

(22) Filed: Jun. 5, 2000

Related U.S. Application Data

(62) Division of application No. 09/109,147, filed on Nov. 12, 1998, now abandoned, which is a division of application No. 08/776,543, filed as application No. PCT/JP96/01547 on Jun. 7, 1996, now Pat. No. 5,877,330.

(30) Foreign Application Priority Data

Jun. 8, 1995 (JP) .................................................. 7-142266

(51) Int. Cl.$^7$ .......................... C07C 255/00; C07C 69/00; C07C 15/02; C07C 2/00; C07C 4/00
(52) U.S. Cl. .......................... 558/303; 560/129; 585/400; 585/500; 585/700
(58) Field of Search .......................... 558/303; 560/129; 585/400, 500, 700

(56) References Cited

U.S. PATENT DOCUMENTS

| | | | |
|---|---|---|---|
| 1,458,478 | * 6/1923 | Gibbs | 502/353 |
| 2,510,803 | 6/1950 | Cooper | 252/464 |
| 4,046,833 | 9/1977 | Hardman | 260/683.3 |
| 4,054,607 | 10/1977 | Matsuoka et al. | 260/600 |
| 4,066,704 | 1/1978 | Harris et al. | 260/604 |
| 4,085,193 | * 4/1978 | Nakajima et al. | 423/239 |
| 4,137,259 | 1/1979 | Van Geem et al. | 562/415 |
| 4,255,285 | * 3/1981 | Engelbach et al. | 502/80 |
| 4,378,309 | 3/1983 | Shaw et al. | 252/469 |
| 4,734,391 | * 3/1988 | Schneider et al. | 502/84 |
| 4,835,126 | 5/1989 | Wachs et al. | 502/209 |
| 4,879,264 | * 11/1989 | Toft et al. | 502/8 |
| 5,558,680 | * 9/1996 | Takeuchi et al. | 29/623.1 |
| 5,686,381 | * 11/1997 | Albonetti et al. | 502/352 |
| 5,877,330 | * 3/1999 | Kishimoto et al. | 549/240 |
| 6,107,234 | * 8/2000 | Bortinger | 502/209 |
| 6,124,233 | * 9/2000 | Abdulwahed et al. | 502/312 |
| 6,124,499 | * 9/2000 | Hibst et al. | 562/535 |
| 6,133,184 | * 10/2000 | Kiyooka et al. | 502/63 |
| 6,143,928 | * 11/2000 | Karim et al. | 562/534 |
| 6,159,887 | * 12/2000 | Trujillo et al. | 502/64 |
| 6,162,760 | * 12/2000 | Brazdil, Jr. | 502/353 |
| 6,166,241 | * 12/2000 | Kayou et al. | 558/318 |
| 6,166,268 | * 12/2000 | Kuehnle et al. | 568/800 |
| 6,174,833 | * 1/2001 | Bertola et al. | 502/209 |

FOREIGN PATENT DOCUMENTS

| | | |
|---|---|---|
| 0 264 747 A1 | 4/1988 | (EP) . |
| 0 339 553 A2 | 11/1989 | (EP) . |
| 0 472 014 A1 | 2/1992 | (EP) . |
| 355192 | 11/1931 | (GB) . |
| 381570 | 10/1932 | (GB) . |
| 838843 | 6/1960 | (GB) . |
| 946583 | 1/1964 | (GB) . |
| 1336136 | 11/1973 | (GB) . |
| 1520336 | 8/1978 | (GB) . |
| 51-21958 | 7/1976 | (JP) . |
| 58-14254 B2 | 3/1983 | (JP) . |
| 60-35180 B2 | 8/1985 | (JP) . |
| 61-18726 | 1/1986 | (JP) . |
| 5-138043 | 6/1993 | (JP) . |
| 5-51344 | 6/1993 | (JP) . |
| 5-221912 | 8/1993 | (JP) . |
| 8-71423 | 3/1996 | (JP) . |
| 90/13352 | 11/1990 | (WO) . |
| 95/05895 | 3/1995 | (WO) . |

OTHER PUBLICATIONS

Smits et al. "Influence of perparaion method on the performance of vanadia–niobia catalysts for the oxidative dehydrogenation of propane" Catalysis Today, vol. 16, May 3, 1993, pp. 513–523, XP002135078.

"Gmelins Handbuch der Anorganischen Chemie; 8. Auflage; Vanadium; Teil B–Lieferung 1; System–number 48; pp. 98–101" Verlag Chemie GmbH, Weinheim XP002135135.

"Gmelins Handbuch der Anorganischen Chemie; 8. Auflage; Vanadium; Teil B–Lieferung 1; System–number 48; pp. 133–134" 1967 Verlag Chemie GmbH, Weinheim XP002135136.

Lemerle et al., "Condensation Process in Polyvanadic Acid Solutions," *J. inorg. nucl. Chem.*, vol. 42, pp. 17–20, (1980).

Pozarnsky et al., Effects of Aging Time on $V_2O_5$ Sol–Gel Coatings, *Journal of Sol–Gel Science and Technology*, 3, pp. 57–62 (1994).

Eon et al., "Oxidative Dehydrogenation of Propane on $\gamma$–$Al_2O_3$ Supported Vanadium Oxides", *Journal of Catalysis*, 145, pp. 318–326, (1994).

* cited by examiner

Primary Examiner—Deborah C. Lambkin
(74) Attorney, Agent, or Firm—Kubovcik & Kubovcik

(57) ABSTRACT

Vanadium-containing catalysts are obtained by using polyvanadic acid as a source of vanadium. Vanadium-containing catalysts are obtained by mixing catalyst components other than vanadium, or their precursors, with a polyvanadic acid sol which is formed by ion-exchanging a metavanadic acid aqueous solution with a proton-type cation-exchange resin and performing polycondensation, and by drying and/or calcining the mixture. Such vanadium-containing catalysts can fully exhibit their catalytic activity under mild reaction conditions, and can be suitably used for various reactions, such as synthesis of phthalic anhydride by the partial oxidation of o-xylene, synthesis of benzaldehyde by the partial oxidation of toluene, synthesis of benzoic acid by the partial oxidation of toluene, synthesis of anisaldehyde by the partial oxidation of p-methoxy toluene, synthesis of propylene by the oxidative dehydrogenation of propane, synthesis of isobutene by the oxidative dehydrogenation of isobutane, synthesis of methyl formate by the oxidative dehydrogenation of methanol, and synthesis of acrylonitrile by the ammoxidation of propane.

19 Claims, No Drawings

VANADIUM-CONTAINING CATALYSTS, PROCESS FOR MANUFACTURING AND USE OF THE SAME

This application is a division of application Ser. No. 09/109,147 filed Nov. 12, 1998, abandoned, which is a division of application Ser. No. 08/776,543 filed Jan. 29, 1997, now U.S. Pat. No. 5,877,330, issued Mar. 2, 1999, and which is the national stage application of International Application No. PCT/JP96/01547 filed Jun. 7, 1996.

TECHNICAL FIELD

The present invention relates to vanadium-containing catalysts used for various types of catalytic reactions, for example, oxidation reactions. More specifically, the present invention relates to catalysts containing vanadium as a principal component, suitable for use in various reactions including oxidation reactions of aromatic hydrocarbon, heterocyclic compound, saturated aliphatic hydrocarbon, unsaturated aliphatic hydrocarbon, and derivatives thereof, for example, various partial oxidation reactions, such as synthesis of phthalic anhydride from o-xylene or naphthalene, synthesis of pyromellitic dianhydride from durene, synthesis of maleic anhydride from benzene or n-butane, synthesis of (substituted) benzaldehyde from (substituted) toluene, synthesis of benzoic acid from toluene, synthesis of pyridine carboxylic acids by the oxidation of picoline, lutidine, quinoline, etc., synthesis of formaldehyde from methane, and synthesis of (meth)acrylic acid from (meth)acrolein; various oxidative dehydrogenation reactions, such as synthesis of propylene and butenes by the oxidative dehydrogenation of propane and butanes, and synthesis of formaldehyde and methyl formate from methanol; various ammoxydation reactions, such as synthesis of benzonitrile by the ammoxydation of toluene, synthesis of acrylonitrile and methacrylonitrile by the ammoxydation of propane and isobutane; oxidation reactions of inorganic compounds, such as synthesis of sulfuric acid by the oxidation of $SO_2$; reductive denitration of nitrogen oxide by means of ammonia; decomposition reactions of organic halides; hydrogenation reactions; dehydrogenation reactions; hydrodesulfurization reactions; isomerization reactions; alkylation reactions; dehydration reactions; polymerization reactions: and photocatalytic reactions. The present invention also relates to a process for manufacturing such catalysts. Furthermore, the present invention relates to processes for manufacturing phthalic anhydride, isobutene, methyl formate, benzaldehyde, benzoic acid, anisaldehyde, propylene and acrylonitrile as the uses of such catalysts.

BACKGROUND ART

Catalysts containing vanadium as a principal component have been studied or industrially used in various reactions, such as synthesis of phthalic anhydride by the oxidation of o-xylene or naphthalene, synthesis of pyromellitic dianhydride by the oxidation of durene, synthesis of maleic anhydride by the oxidation of benzene or n-butane, synthesis of benzonitrile by the ammoxydation of toluene, synthesis of substituted benzaldehyde by the oxidation of substituted toluene, synthesis of acrylic acid by the oxidation of acrolein, synthesis of formaldehyde by the oxidative dehydrogenation of methanol, synthesis of propylene and butenes by the oxidative dehydrogenation of propane and butanes, synthesis of acrylonitrile and methacrylonitrile by the ammoxydation of propane and isobutane, synthesis of sulfuric acid by the oxidation of $SO_2$, reductive denitration of nitrogen oxide by means of ammonia, and decompositions reaction of organic halides.

In the above-mentioned conventional catalysts, vanadium presents in the form of oxide or composite oxide with other component. Vanadium is often used as a molded catalyst prepared by molding such oxide or composite oxide, or a supported catalyst containing such oxide or composite oxide supported on a carrier. The preparation of such a catalyst has been carried out by using an aqueous solution of water-soluble salt like ammonium metavanadate and vanadyl oxalate, or an aqueous solution obtained by dissolving such a water-soluble salt or vanadium pentoxide in an oxalic acid and a mineral acid such as hydrochloric acid; impregnating a carrier with the solution, or mixing the solution with other component.

However, since the conventional vanadium-containing catalysts are formed by only compulsory deposition of a vanadium component on a carrier or solidifying a vanadium component, for example, by evaporating and drying a solution containing vanadium component, and therefore the interaction with the carrier or other component is weak. Hence, non-uniformity of supported component and nonhomogeneous mixing are unavoidable due to the movement of substances during drying. Thus, the conventional vanadium-containing catalysts cannot achieve sufficient catalytic performance because of poor dispersion, uniformity and thermal stability of an active catalyst component having catalytic activity, insufficient reaction yield and catalyst life.

For example, phthalic anhydride is synthesized by the oxidation of o-xylene using a catalyst system for which $V_2O_5$—$TiO_2$ are essential. In this case, in ideal, the use of a catalyst system having a monolayer of $V_2O_5$ on the surface of anatase type titania is preferred. However, in the conventional process for manufacturing catalysts, it is difficult to achieve such an ideal dispersion state.

A reductive denitration of $NO_x$ is performed by $NH_3$ over the catalyst system containing $V_2O_5$—$TiO_2$. However, in this case, the catalyst obtained by the conventional manufacturing process also faces a limitation in its thermal stability. Namely, such a catalyst can be used in a low-temperature range, but cannot be used in a high-temperature range exceeding 500° C.

For example, it is known that a catalyst system containing V—Mg composite oxide is effective for the oxidative dehydrogenation of propane and butanes. In a prior art, an effective phase formation is performed by calcining the solid phase at high temperatures in the final stage. However, like the above-mentioned case, the control of the phase formation is extremely difficult due to the non-uniformity of mixing of components. Thus, this catalyst system has not reached an industrially implementable level.

Moreover, in the conventional process for manufacturing a vanadium-containing catalyst, calcination at high temperatures is essential to remove residues like residues of vanadates and organic substances used as starting materials, thereby restricting the preparation conditions of catalysts. Consequently, the performance of the catalysts is limited.

As special preparation methods, a sol-gel method using vanadyl alkoxide, a liquid-phase deposition method using $VOCl_3$, and a CVD (Chemical Vapor Deposition) method are listed. However, these methods require expensive starting materials or a special device, and are not suitable for mass-production. Hence, these methods have not been put to practical use.

Hence, vanadium-containing catalysts that achieve excellent dispersion, uniformity and thermal stability and high catalytic performance are required for various reactions. The present invention was implemented to solve the above-mentioned conventional problems, and its object is to provide novel vanadium-containing catalysts achieving excellent dispersion, uniformity and thermal stability, and high catalytic performance for various reactions. It is another object of the present invention to provide a process for manufacturing a vanadium-containing catalyst achieving excellent dispersion, uniformity and thermal stability, and high catalytic performance. It is still another object of the present invention to provide a process for efficiently manufacturing phthalic anhydride, isobutene, methyl formate, benzaldehyde, benzoic acid, anisaldehyde, propylene, or acrylonitrile by means of a vanadium-containing catalyst.

DISCLOSURE OF INVENTION

The present inventors eagerly studied to provide novel vanadium-containing catalysts. It was found through the study that polyvanadic acid performs a strong adsorption function, is tightly bonded to a solid surface or colloid particles and forms a stable compound with other metal because of its strong reactivity. Therefore, polyvanadic acids were applied to the manufacture of vanadium-containing catalysts. As a result, it was found that vanadium-containing catalysts obtained by using polyvanadic acid as a source of vanadium achieve excellent dispersion, uniformity and thermal stability, and are suitable for use in various reactions including oxidation reactions of aromatic hydrocarbon, heterocyclic compound, saturated aliphatic hydrocarbon, unsaturated aliphatic hydrocarbon, and derivatives thereof, for example, various partial oxidation reactions, such as synthesis of phthalic anhydride from o-xylene or naphthalene, synthesis of pyromellitic dianhydride from durene, synthesis of maleic anhydride from benzene or n-butane, synthesis of (substituted) benzaldehyde from (substituted) toluene, synthesis of benzoic acid from toluene, synthesis of pyridine carboxylic acids by the oxidation of picoline, lutidine, quinoline, etc., synthesis of formaldehyde from methane, and synthesis of (meth)acrylic acid from (meth)acrolein; various oxidative dehydrogenation reactions, such as synthesis of propylene and butenes by the oxidative dehydrogenation of propane and butanes, and synthesis of formaldehyde and methyl formate from methanol; various ammoxydation reactions, such as synthesis of benzonitrile by the ammoxydation of toluene, synthesis of acrylonitrile and methacrylonitrile by the ammoxydation of propane and isobutane; oxidation reactions of inorganic compounds, such as synthesis of sulfuric acid by the oxidation of $SO_2$; reductive denitration of nitrogen oxide by means of ammonia; decomposition reactions of organic halides; hydrogenation reactions; dehydrogenation reactions; hydrodesulfurization reactions; isomerization reactions; alkylation reactions; dehydration reactions; polymerization reactions: and photocatalytic reactions. The present invention was completed based on the results of the study.

More specifically, in order to achieve the above objects, vanadium-containing catalysts of the present invention are characterized in using polyvanadic acid as a source of vanadium. In this structure, it is preferred that the polyvanadic acid is used together with catalyst components other than vanadium, or their precursors.

The catalyst components other than vanadium, or their precursors are preferably compounds of at least one element selected from the group consisting of Ti, Zr, Nb, Ta, Cr, Mo, W, Mn, Re, Fe, Co, Ni, Ru, Rh, Pd, Ir, Pt, Cu, Ag, Zn, B, Al, Ga, In, Tl, Si, Ge, Sn, Pb, P, Sb, Bi, Se, Te, Na, K, Rb, Cs, Mg, Ca, La and Ce.

Moreover, at least one of the catalyst components other than vanadium, or their precursors, is preferably an inorganic porous substance. A preferred inorganic porous substance is metal oxide and/or metal hydroxide. The metal oxide and/or the metal hydroxide is preferably oxide and/or hydroxide of at least one metal selected from the group consisting of Ti, Zr, Nb, Al, Si, Sn, Sb, Mo, W, Mn, Ce and Mg. The metal oxide and/or the metal hydroxide is more preferably oxide and/or hydroxide of at least one metal selected from the group consisting of Ti, Zr, Nb, Al, Si and Mg.

Furthermore, it is preferred that the polyvanadic acid is formed by ion-exchanging a metavanadate aqueous solution with a proton-type cation-exchange resin, and then performing polycondensation.

In order to achieve the above-mentioned objects, the vanadium-containing catalysts of the present invention are prepared by mixing catalyst components other than vanadium, or their precursors, with a polyvanadic acid sol, which is formed by ion-exchanging a metavanadate aqueous solution with a proton-type cation-exchange resin and performing polycondensation, and then drying and/or calcining the mixture.

Compared to conventional vanadium-containing catalysts, the vanadium-containing catalysts of the above-mentioned structure achieve excellent dispersion, uniformity and thermal stability, and have excellent catalytic performance and longer life. Hence, such vanadium-containing catalysts can fully exhibit their catalytic activity under mild reaction conditions, and are suitable for use in various reactions including oxidation reactions of aromatic hydrocarbon, heterocyclic compound, saturated aliphatic hydrocarbon, unsaturated aliphatic hydrocarbon, and derivatives thereof, for example, various partial oxidation reactions, such as synthesis of phthalic anhydride from o-xylene or naphthalene, synthesis of pyromellitic dianhydride from durene, synthesis of maleic anhydride from benzene or n-butane, synthesis of (substituted) benzaldehyde from (substituted) toluene, synthesis of benzoic acid from toluene, synthesis of pyridine carboxylic acids by the oxidation of picoline, lutidine, quinoline, etc., synthesis of formaldehyde from methane, and synthesis of (meth)acrylic acid from (meth)acrolein; various oxidative dehydrogenation reactions, such as synthesis of propylene and butenes by the oxidative dehydrogenation of propane and butanes, and synthesis of formaldehyde and methyl formate from methanol; various ammoxydation reactions, such as synthesis of benzonitrile by the ammoxydation of toluene, and synthesis of acrylonitrile and methacrylonitrile by the ammoxydation of propane and isobutane; oxidation reactions of inorganic compounds, such as synthesis of sulfuric acid by the oxidation of $SO_2$; reductive denitration of nitrogen oxide by means of ammonia; decomposition reactions of organic halides; hydrogenation reactions; dehydrogenation reactions; hydrodesulfurization reactions; isomerization reactions; alkylation reactions; dehydration reactions; polymerization reactions: and photocatalytic reactions.

The following description will discuss the summary of the process for manufacturing a vanadium-containing catalyst of the present invention. First, an aqueous solution is formed by dissolving vanadate in water. Subsequently, by passing the aqueous solution through an ion-exchange resin column, a proton-type vanadic acid aqueous solution is formed. Next, the proton-type vanadate aqueous solution undergoes polycondensation to give a polyvanadic acid as one form of the precursor of the vanadium-containing catalyst of the present invention.

The co-existence of polyvanadic acid and catalyst components other than vanadium, or their precursors is allowed in some cases, for example, by means of mixing, kneading, co-precipitating, or depositing the polyvanadic acid and catalyst components other than vanadium, or their precursors. Such an arrangement allows the co-existence or composite of the polyvanadic acid and catalyst components other than vanadium, or their precursors.

Vanadium-containing catalysts are obtained by drying and calcining the precursors of vanadium-containing catalysts using polyvanadic acid formed by the above-mentioned processing steps according to the need.

Furthermore, the above-mentioned catalysts can be prepared in a desired form according to a reaction in which the catalysts are to be used, by molding and classifying the precursors in a desired shape and particle size.

The above-mentioned process is merely the summary, and the means may be suitably varied by changing the types and concentrations of the starting materials, the ion-exchange resin, and the reaction and co-existence conditions. The following description will discuss the preparation steps and starting materials in detail.

In order to solve the above-mentioned problems, a process for manufacturing a vanadium-containing catalyst of the present invention includes the steps of:

mixing a polyvanadic acid and catalyst components other than vanadium, or their precursors; and drying and/or calcining the resultant mixture.

This process allows the manufacture of vanadium-containing catalysts which achieve higher catalytic activity, longer life, excellent dispersion and thermal stability compared to conventional vanadium-containing catalysts, and do not deteriorate even when used at high temperatures. Thus, the vanadium-containing catalysts according to the present invention can fully exhibit their catalytic activity under mild reaction conditions, and are suitable for use in various reactions mentioned above.

In order to solve the above-mentioned problems, a process for manufacturing phthalic anhydride of the present invention is characterized in contacting a mixed gas containing o-xylene, and molecular oxygen such as oxygen, air and a mixed gas of oxygen and inactive gas, with a vanadium-containing catalyst obtained by using polyvanadic acid as a source of vanadium. This process allows an efficient manufacture of phthalic anhydride.

In order to solve the above-mentioned problems, a process for manufacturing isobutene of the present invention is characterized in contacting a mixed gas containing isobutane and molecular oxygen with a vanadium-containing catalyst obtained by using polyvanadic acid as a source of vanadium. This process allows an efficient manufacture of isobutene.

In order to solve the above-mentioned problems, a process for manufacturing methyl formate of the present invention is characterized in contacting a mixed gas containing methanol and molecular oxygen with a vanadium-containing catalyst obtained by using polyvanadic acid as a source of vanadium. This process allows an efficient manufacture of methyl formate.

In order to solve the above-mentioned problems, a process for manufacturing benzaldehyde of the present invention is characterized in contacting a mixed gas containing toluene and molecular oxygen with a vanadium-containing catalyst obtained by using polyvanadic acid as a source of vanadium. This process allows an efficient manufacture of benzaldehyde.

In order to solve the above-mentioned problems, a process for manufacturing benzoic acid of the present invention is characterized in contacting a mixed gas containing toluene and molecular oxygen with a vanadium-containing catalyst obtained by using polyvanadic acid as a source of vanadium. This process allows an efficient manufacture of benzoic acid.

In order to solve the above-mentioned problems, a process for manufacturing anisaldehyde of the present invention is characterized in contacting a mixed gas containing p-methoxy toluene and molecular oxygen with a vanadium-containing catalyst obtained by using polyvanadic acid as a source of vanadium. This process allows an efficient manufacture of anisaldehyde.

In order to solve the above-mentioned problems, a process for manufacturing propylene of the present invention is characterized in contacting a mixed gas containing propane and molecular oxygen with a vanadium-containing catalyst obtained by using polyvanadic acid as a source of vanadium. This process allows an efficient manufacture of propylene.

In order to solve the above-mentioned problems, a process for manufacturing acrylonitrile of the present invention is characterized in contacting a mixed gas containing propane, molecular oxygen, and ammonia with a vanadium-containing catalyst obtained by using polyvanadic acid as a source of vanadium. This process allows an efficient manufacture of acrylonitrile.

The present invention will be discussed in detail below. In this invention, the term "polyvanadic acid" means polyacid formed by the polycondensation of at least two, preferably 10 or more vanadic acids ($HVO_3$). The term "(substituted)" means that a substituent group may be contained or may not be contained.

The vanadium-containing catalysts of the present invention are obtained by using polyvanadic acid as a source of vanadium.

In order to remove impurities such as residues of vanadates and organic substances used as starting materials, it is preferred that the polyvanadic acid is formed by ion-exchanging an vanadic acid aqueous solution with a proton-type cation-exchange resin, and then performing polycondensation.

Although the vanadate is not particularly limited, preferred vanadate ions (anions) are metavanadate ions and preferred counter ions (cations) are alkali metal ions and/or ammonium ions. Specific examples of the vanadate are ammonium metavanadate, sodium metavanadate, and potassium metavanadate.

The concentration of the vanadic acid aqueous solution is not particularly limited, but the lower limit of vanadium ion is preferably 0.01 moles/l, more preferably 0.03 moles/l, and most preferably 0.05 moles/l. When the concentration of the vanadic acid aqueous solution is lower than 0.01 moles/l, the rate of polymerization reaction of vanadic acid is lowered, and it takes too much time for the preparation of polyvanadic acid. The upper limit indicates the amount of vanadates that dissolve in a saturated state in water. For example, in an ammonium metavanadic acid aqueous solution, the upper limit is approximately 0.8 moles/l, preferably 0.4 moles/l, and more preferably 0.2 moles/l.

The method of ion-exchanging the vanadic acid aqueous solution with a proton-type cation-exchange resin is not particularly limited. For example, the cation-exchange is carried out by dropping the vanadic acid aqueous solution on the proton-type cation-exchange resin column or passing the vanadic acid aqueous solution through the proton-type cation-exchange resin so as to bring them into contact with each other. In this method, the proton-type vanadic acid aqueous solution is readily obtained. Although the type of proton-type cation-exchange resin is not particularly limited, a strong acidic proton-type cation-exchange resin is preferred. The treatment conditions such as time and temperature are not particularly limited. The above-mentioned proton-type cation-exchange resin can be used repeatedly by applying, for example, a regenerating treatment with hydrochloric acid.

Immediately after the ion-exchange process, most of the vanadic acids formed by the ion exchange are turned into decavanadic acid which is formed by the polycondensation of ten vanadic acids. It is possible to use the decavanadic acid as the polyvanadic acid. However, it is preferred to use the decavanadic acid after arranging it to undergo further polycondensation.

When the polycondensation proceeds, colloid particles of polyvanadic acid are formed, and the polyvanadic acid turns into the sol state. The colloid particles have a particle diameter of at least 10 Å, and the average number of vanadium atoms constituting one colloid particle is not less than 1000. When about 80% of the total vanadium atoms in the system form the colloid particles (the remaining about 20% of the vanadium atoms are present as the decavanadate), a polyvanadic acid sol with stable composition is obtained, and is suitably used for the preparation of the catalysts of the present invention.

The reaction conditions in performing the polycondensation of the vanadic acid aqueous solution formed by the ion exchange are not particularly limited. For example, the polycondensation spontaneously proceeds by leaving the vanadic acid at room temperature for a long time. The polymerization rate can be increased by heating the vanadic acid. In the case of heating, preferred reaction temperatures are not higher than 10° C.

The reaction time for obtaining the polyvanadic acid sol with stable composition varies depending on the reaction temperature and the concentration of the vanadic acid aqueous solution. For example, in the case of polycondensation at room temperature, the reaction time is preferably not shorter than one day, more preferably not shorter than seven days. For example, in the case of polycondensation at 80° C., about three to four hours is sufficient as the reaction time. The polyvanadic acid sol with stable composition is readily obtained under these reaction conditions.

If the concentration of the vanadic acid formed by the ion exchange exceeds 0.2 moles/l, when the polycondensation proceeds, the polyvanadic acid in the gel state is obtained. It is possible to use the gel for the preparation of the catalyst of the present invention. However, it is preferred to use the polyvanadic acid in the sol state by dispersing the gel in water.

The use of the polyvanadic acid as a source of vanadium is not particularly limited. However, it is preferred to use the polyvanadic acid together with catalyst components other than vanadium, or their precursors. The catalyst components other than vanadium, or their precursors are preferably compounds of at least one element selected from the group consisting of Ti, Zr, Nb, Ta, Cr, Mo, W, Mn, Re, Fe, Co, Ni, Ru, Rh, Pd, Ir, Pt, Cu, Ag, Zn, B, Al, Ga, In, Tl, Si, Ge, Sn, Pb, P, Sb, Bi, Se, Te, Na, K, Rb, Cs, Mg, Ca, La and Ce.

The use of the polyvanadic acid as a source of vanadium together with the catalyst components other than vanadium, or their precursors, is not particularly limited. Preferred uses include: impregnating an inorganic porous substance as a catalyst component with an aqueous solution or sol of polyvanadic acid; mixing the aqueous solution or sol of polyvanadic acid with a gel or sol of the precursor of the inorganic porous substance; and mixing the aqueous solution or sol of polyvanadic acid with a uniform solution of catalyst components.

As the process for manufacturing a vanadium-containing catalyst of the present invention, a preferred process includes mixing the polyvanadic acid sol with catalyst components other than vanadium, or their precursors, and drying and/or calcining the mixture.

When using the polyvanadic acid sol for the preparation of the vanadium-containing catalysts of the present invention, the polyvanadic acid sol can be used directly or after being condensed. It is also possible to use the polyvanadic acid sol after diluting it with water or other solvent.

At least one of the catalyst components other than vanadium (hereinafter just referred to as the catalyst components), or their precursors is preferably an inorganic porous substance. An example of an inorganic porous substance is a heat-resistant inactive substance which is generally called a carrier. However, the catalyst components, or their precursors are not necessarily limited to this substance. Namely, the catalyst components other than vanadium, or their precursors include a substance that performs catalytic activity, or a substance that forms a composite compound with vanadium.

The compounds that form the inorganic porous substance are not particularly limited. Examples of such compounds include metal oxide, metal hydroxide, nitride, and carbide. Among these compounds, metal oxides and/or metal hydroxide are particularly preferred. The specific surface area of the inorganic porous substance is not particularly limited, but is preferably between 0.1 $m^2/g$ and 1000 $m^2/g$, more preferably between 1 $m^2/g$ and 500 $m^2/g$.

The metal oxide and/or metal hydroxide are not particularly limited, but are preferably oxide and/or hydroxide of at least one metal selected from the group consisting of Ti, Zr, Nb, Al, Si, Sn, Sb, Mo, W, Mn, Ce, and Mg, and more preferably oxide and/or hydroxide of at least one metal selected from the group consisting of Ti, Zr, Nb, Al, Si, and Mg. In the present invention, the inorganic porous substance includes the precursors of these metal oxide and hydroxide. For example, the precursors are the sol or gel of the hydrates of these metal compounds, or metal compounds in the slurry state, which turn into inorganic porous substances by drying, calcining, etc.

When preparing the vanadium-containing catalysts of the present invention by using the sol or aqueous solution of polyvanadic acid together with the inorganic porous substance, if heating is applied, the adsorption function of the polyvanadic acid is promoted, thereby producing favorable results. Similarly, if heating is performed when using the sol or aqueous solution of polyvanadic acid together with catalyst components, the reaction with the polyvanadic acid is promoted, thereby producing favorable results. The heating temperature is not particularly limited, but preferred temperatures for producing sufficient effects are between 50° C. and 100° C.

The vanadium-containing catalysts of the present invention may contain catalyst components other than the inorganic porous substance (hereinafter just referred to as the "other catalyst components"). The metal for forming the other catalyst components are not particularly limited if it is at least one metal selected from the group consisting of Ti, Zr, Nb, Ta, Cr, Mo, W, Mn, Re, Fe, Co, Ni, Ru, Rh, Pd, Ir, Pt, Cu, Ag, Zn, B, Al, Ga, In, Tl, Si, Ge, Sn, Pb, P, Sb, Bi, Se, Te, Na, K, Rb, Cs, Mg, Ca, La, and Ce. The co-existence of the such a metal compound with vanadium can improve the catalytic performance of the vanadium-containing catalyst.

Specific examples of the other catalyst components or their precursors used for the introduction of the other catalyst components, include: non-porous solids, such as calcined silicon carbide; solutions of various metal salts, such as nitrate, sulfate, acetate, and chloride; organic metal compounds; metal alkoxide; liquid or gaseous compounds of metal chlorides, etc.

The method of introducing these other catalyst components is not particularly limited. For example, the aqueous solution or sol of polyvanadic acid is mixed with these other catalyst components or their precursors, and then the mixed solution is brought into contact with the inorganic porous substance. As another example, the sol or aqueous solution of polyvanadic acid is arranged to be supported on the inorganic porous substance in advance by the above-mentioned method, and then soaked in a solution containing the other catalyst components or their precursors. In the latter case, since the adsorptively supported polyvanadic acid is firmly fixed to the inorganic porous substance, it is not affected, i.e., dropped nor moved, in the following step of introducing the other catalyst components.

The vanadium-containing catalysts of the present invention are obtained by drying and/or calcining polyvanadic acid itself, or the mixture of polyvanadic acid and catalyst components other than vanadium or their precursors.

The drying temperature is not particularly limited, but is preferably not lower than 0° C. but is lower than 150° C., more preferably between 20° C. and 120° C. The calcination temperature is not particularly limited, but is preferably between 150° C. and 1000° C., more preferably between 200° C. and 800° C. The atmosphere for drying and calcining is not particularly limited. However, drying and calcining are normally performed under air or nitrogen atmosphere.

When drying (and calcining), if the polyvanadic acid is formed by the above-mentioned ion-exchange, since useless residues and organic substances are not contained, it is not necessary to perform calcining at high temperatures for removing such residues and organic substances. In this case, a sufficient catalytic function is obtained by only drying, and the resultant catalyst is suitable for use. Thus, the limitations of the drying (and calcining) temperatures are eliminated, and an optimum temperature can be selected from a wide temperature range according to, for example, the use of the catalyst.

On the other hand, if polyvanadic acid is not the one obtained by the ion-exchange, the polyvanadic acid contains useless residues and organic substances. It is therefore necessary to perform calcining at high temperatures for removing such residues and organic substances.

The vanadium content of the vanadium-containing catalyst of the present invention is not particularly limited. However, if the amount of vanadium contained in the vanadium-containing catalyst is expressed in terms of the weight of $V_2O_5$, the vanadium content is preferably in a range of 0.1% to 80% by weight based on the total weight of the vanadium-containing catalyst, and more preferably in a range of 0.3% to 50% by weight.

The shape of the vanadium-containing catalyst is not particularly limited. When using the vanadium-containing catalyst as a fixed-bed, it is preferred to mold the vanadium-containing catalyst into a predetermined shape according to the shape of the reaction tube, or to crush the molding into a grain size of a suitable mesh.

The vanadium-containing catalysts of the present invention fully exhibit their catalytic activity under mild reaction conditions for various reactions, including: various oxidation reactions, such as partial oxidation of organic substances, oxidative dehydrogenation of organic substances, ammoxydation of organic substances; partial oxidation of inorganic substances, for example, synthesis of sulfuric acid by the oxidation of sulfur dichloride $(SO_2 \rightarrow SO_3(\rightarrow H_2SO_4))$; reductive denitration of nitrogen oxide by means of ammonia $(NO_x+NH_3 \rightarrow N_2,H_2O)$; hydrogenation reactions of organic substances like the hydrocracking of petroleum (crude petroleum); dehydrogenation reactions (not oxidative) of organic substances; hydrodesulfurization reactions of organic substances like a hydrodesulfurization reaction of petroleum; decomposition reactions of organic halides $(RX \rightarrow CO_2, H_2O, HX, X_2$, etc.); isomerization reactions of organic substances; alkylation reactions of organic substances; dehydration reactions of alcohols; polymerization reactions of organic substances like polymerization of styrene and polymerization of 1-butene: photocatalytic reactions of organic substances like synthesis of acetone from propane and synthesis of acrolein from propylene; and photocatalytic reactions of inorganic substances like decomposition of nitrogen monoxide $(NO \rightarrow N_2, O_2)$.

Examples of the partial oxidation of organic substances include partial oxidation of aromatic hydrocarbon, partial oxidation of heterocyclic compound, partial oxidation of saturated aliphatic hydrocarbon, partial oxidation of unsaturated aliphatic hydrocarbon, and partial oxidation of the derivatives of these compounds.

Specific examples of the partial oxidation of the aromatic hydrocarbon are synthesis of phthalic anhydride by the partial oxidation of o-xylene, synthesis of phthalic anhydride by the partial oxidation of naphthalene, synthesis of pyromellitic dianhydride by the partial oxidation of durene, synthesis of maleic anhydride by the partial oxidation of benzene, synthesis of (substituted) benzaldehydes like benzaldehyde and anisaldehyde by the partial oxidation of (substituted) toluenes such as toluene and p-methoxy toluene, synthesis of (substituted) benzoic acids like benzoic acid and p-hydroxy benzoic acid by the partial oxidation of (substituted) toluenes such as toluene and p-hydroxy toluene, synthesis of benzoquinone by the partial oxidation of benzene, synthesis of naphthoquinone by the partial oxidation of naphthalene, and synthesis of anthraquinone by the partial oxidation of anthracene, and synthesis of phenol by the partial oxidation of benzene.

Specific examples of the partial oxidation of heterocyclic compound are synthesis of pyridine carboxylic acids by the partial oxidation of heterocyclic compounds having a pyridine skeleton, such as picoline, lutidine, and quinoline.

Specific examples of the partial oxidation of the saturated aliphatic hydrocarbon are synthesis of formaldehyde by the partial oxidation of methane, synthesis of methanol by the partial oxidation of methane, synthesis of acetaldehyde by the partial oxidation of ethane, synthesis of acetic acid by the partial oxidation of ethane, synthesis of acrolein by the partial oxidation of propane, synthesis of acrylic acid by the partial oxidation of propane, synthesis of maleic anhydride by the oxidation of n-butane, synthesis of methacrolein by the partial oxidation of isobutane, and synthesis of methacrylic acid by the partial oxidation of isobutane.

Specific examples of the partial oxidation of the unsaturated aliphatic hydrocarbon are synthesis of acetaldehyde by the partial oxidation of ethylene, synthesis of acetone by the partial oxidation of propylene, synthesis of acrolein by the partial oxidation of propylene, synthesis of maleic anhydride by the partial oxidation of n-butane, synthesis of maleic anhydride by the partial oxidation of butadiene, and synthesis of methacrolein by the partial oxidation of isobutene.

Specific examples of the partial oxidation of the derivatives of the above-mentioned compounds (aromatic hydrocarbon, heterocyclic compound, saturated aliphatic hydrocarbon, and unsaturated aliphatic hydrocarbon) are partial oxidation of aldehyde, such as synthesis of acrylic acid by the partial oxidation of acrolein, synthesis of methacrylic acid by the partial oxidation of methacrolein, and synthesis of maleic anhydride by the partial oxidation furfural.

Examples of the partial oxidative dehydrogenation of the organic substances include oxidative dehydrogenation of aromatic hydrocarbon, oxidative dehydrogenation of heterocyclic compound, oxidative dehydrogenation of saturated aliphatic hydrocarbon, oxidative dehydrogenation of unsaturated aliphatic hydrocarbon, and oxidative dehydrogenation of the derivatives of thereof.

Specific examples of the oxidative dehydrogenation of aromatic hydrocarbon are synthesis of alkenyl benzene by the oxidative dehydrogenation of alkyl benzene like synthesis of styrene by the oxidative dehydrogenation of ethylbenzene, and synthesis of alkenyl naphthalene by the oxidative dehydrogenation of alkyl naphthalene.

Specific examples of the oxidative dehydrogenation of heterocyclic compound are synthesis of alkenyl pyridine by the oxidative dehydrogenation of alkyl pyridine such as picoline and lutidine.

Specific examples of the oxidative dehydrogenation of saturated aliphatic hydrocarbon are synthesis of ethylene by the oxidative dehydrogenation of ethane, synthesis of propylene by the oxidative dehydrogenation of propane, synthesis of butenes by the oxidative dehydrogenation of n-butane, and synthesis of isobutene by the oxidative dehydrogenation of isobutane.

A specific example of the oxidative dehydrogenation of unsaturated aliphatic hydrocarbon is synthesis of butadiene by the oxidative dehydrogenation of butene.

Specific examples of the oxidative dehydrogenation of the derivatives of the above-mentioned compounds include: oxidative dehydrogenation of alcohols, such as synthesis of methyl formate by the oxidative dehydrogenation of methanol (oxidative dehydrogenation dimerization reaction), synthesis of formaldehyde by the oxidative dehydrogenation of methanol, and synthesis of acetaldehyde by the oxidative dehydrogenation of ethanol; synthesis of pyruvate by the oxidation of lactate; and synthesis of methacrylate by the oxidation of isobutyrate.

Examples of the ammoxydation of organic substances include ammoxidation of aromatic hydrocarbon, ammoxidation of heterocyclic compound, ammoxidation of saturated aliphatic hydrocarbon, and ammoxidation of unsaturated aliphatic hydrocarbon.

Specific examples of the ammoxidation of aromatic hydrocarbon are synthesis of benzonitrile by the ammoxydation of benzene, and synthesis of phthalonitrile by the ammoxydation of xylene.

A specific example of the ammoxidation of heterocyclic compound is synthesis of cyanopyridine by the ammoxydation of picoline, lutidine, etc.

Specific examples of the ammoxidation of saturated aliphatic hydrocarbon are synthesis of acrylonitrile by the ammoxydation of propane, and synthesis of methacrylonitrile by the ammoxydation of isobutane.

Specific examples of the ammoxidation of unsaturated aliphatic hydrocarbon are synthesis of acrylonitrile by the ammoxydation of propylene, and synthesis of methacrylonitrile by the ammoxydation of isobutene.

Among the above-exemplified reactions, the vanadium-containing catalysts of the present invention are suitable for the partial oxidation of aromatic hydrocarbon, partial oxidation of heterocyclic compound, partial oxidation of saturated aliphatic hydrocarbon, partial oxidation of aldehyde, oxidative dehydrogenation of saturated aliphatic hydrocarbon, oxidative dehydrogenation of alcohol, ammoxidation of aromatic hydrocarbon, ammoxidation of saturated aliphatic hydrocarbon, oxidation of sulfur dioxide (synthesis of sulfuric acid), reductive denitration of nitrogen oxide by means of ammonia, and decomposition reactions of organic halides. Among these reactions, the vanadium-containing catalysts of the present invention are particularly suitable for the partial oxidation of aromatic hydrocarbon, partial oxidation of saturated aliphatic hydrocarbon, oxidative dehydrogenation of alcohol, ammoxidation of aromatic hydrocarbon, ammoxidation of saturated aliphatic hydrocarbon, oxidation of sulfur dioxide (synthesis of sulfuric acid), reductive denitration of nitrogen oxide by means of ammonia, and decomposition reactions of organic halides.

Further, among these reactions, the vanadium-containing catalysts of the present invention are most suitable for the synthesis of phthalic anhydride by the partial oxidation of o-xylene, synthesis of benzaldehyde by the partial oxidation of toluene, synthesis of benzoic acid by the partial oxidation of toluene, synthesis of anisaldehyde by the partial oxidation of p-methoxy toluene, synthesis of propylene by the oxidative dehydrogenation of propane, synthesis of isobutene by the oxidative dehydrogenation of isobutane, synthesis of methyl formate by the oxidative dehydrogenation of methanol, and synthesis of acrylonitrile by the ammoxidation of propane.

More specifically, phthalic anhydride is efficiently manufactured by the process of contacting a mixed gas containing o-xylene and molecular oxygen with a vanadium-containing catalyst of the present invention. Benzaldehyde is efficiently manufactured by the process of contacting a mixed gas containing toluene and molecular oxygen with a vanadium-containing catalyst of the present invention. Benzoic acid is efficiently manufactured by the process of contacting a mixed gas containing toluene and molecular oxygen with a vanadium-containing catalyst of the present invention. Anisaldehyde is efficiently manufactured by the process of contacting a mixed gas containing p-methoxy toluene and molecular oxygen with a vanadium-containing catalyst of the present invention. Methyl formate is efficiently manufactured by the process of contacting a mixed gas containing methanol and molecular oxygen with a vanadium-containing catalyst of the present invention.

Propylene is efficiently manufactured by the process of contacting a mixed gas containing propane and molecular oxygen with a vanadium-containing catalyst of the present invention. Isobutene is efficiently manufactured by the process of contacting a mixed gas containing isobutane and molecular oxygen with a vanadium-containing catalyst of the present invention.

Acrylonitrile is efficiently manufactured by the process of contacting a mixed gas containing propane, molecular oxygen and ammonia with a vanadium-containing catalyst of the present invention.

A reactor used for performing various reactions using the above-mentioned vanadium-containing catalysts is not particularly limited. A preferred example is a fixed-bed flow reactor. The reaction conditions, such as temperature, pressure, substrate concentration, flow rate, and amount of catalyst, in performing various reactions are not particularly limited.

Still another objects, characteristics, and advantages of the present invention would be fully understood from the following description. Furthermore, the benefits of the present invention will be clearly explained below.

BEST MODE FOR IMPLEMENTING THE INVENTION

The following description will discuss the present invention in greater detail with reference to examples and comparable examples. However, the present invention is not limited to these examples.

The conversion of substrates, the selectivity of products, and the yield of products are defined as follows.

Conversion (mole %)=(number of moles of reacted substrate/number of moles of supplied substrate)×100

Selectivity (mole %)=(number of moles of products/number of moles of reacted substrate)×(number of carbons of products/number of carbons of supplied substrate)×100

Yield (mole %)=(conversion×selectivity)/100

EXAMPLE 1

A proton-type vanadic acid aqueous solution was prepared by passing an ammonium metavanadic acid aqueous solution (concentration=1.5 moles/l) as an vanadic acid aqueous solution through a column of cation-exchange resin (DOWEX® available from Dow Chemical Company, 50W-X4, 50 to 100 mesh) so as to perform a cation-exchange. Thereafter, the vanadic acid was left at room temperature for two weeks to polycondense spontaneously. As a result, a dark red polyvanadic acid sol of high viscosity was obtained.

Subsequently, 152 ml of the polyvanadic acid sol was diluted with water to 200 ml. Next, 50 g of anatase-type titanium dioxide powder as an inorganic porous substance (special grade, Wako Pure Chemical Industries, Ltd., specific surface area=19 m$^2$/g) was added to the sol, agitated at 70° C. for four hours, heated to 90° C., and continued to be agitated while evaporating moisture so as to form a paste-like composition. The composition was dried at 100° C. over one night. The composition was calcined at 250° C. for two hours, and then at 500° C. for four hours to give a vanadium-containing catalyst. It was found by analyzing the resultant vanadium-containing catalyst in a predetermined method that the catalyst contained vanadium in an amount corresponding to 4.0% $V_2O_5$ by weight.

Next, synthesis of phthalic anhydride was carried out by the oxidation of o-xylene using the vanadium-containing catalyst. More specifically, first, grains of the vanadium-containing catalyst are arranged into sizes ranging from 9 mesh to 16 mesh. Subsequently, in order to perform a reaction by a fixed-bed flow method, a stainless steel reaction tube with an inner diameter of 10 mm was filled with 4.08 g of the vanadium-containing catalyst. Thereafter, the air containing 1.2% of o-xylene was arranged to pass through the reaction tube at a rate of 250 ml/min. The reaction was performed under conditions of normal pressures and a temperature of 320° C.

After the passage of eight hours from the initiation of the reaction, the reaction gas, i.e., the air passed through the reaction tube, was sampled for 30 minutes, and the product was analyzed using gas chromatography. According to the results of analysis, the conversion of o-xylene was 99.5%, the selectivity of phthalic anhydride as the product was 73.6%, and the yield was 73.2%.

Comparative Example 1

A comparative vanadium-containing catalyst was prepared by a known method. More specifically, 200 ml of water was added to 2.68 g of ammonium metavanadate, heated and agitated into slurry. Subsequently, by gradually adding 5.77 g of oxalic acid to the slurry, a green-blue homogenous aqueous solution was obtained. Thereafter, 50 g of the anatase-type titanium dioxide powder used in Example 1 was added, and treated in the same manner as in Example 1 to produce the comparative vanadium-containing catalyst. The resultant comparative vanadium-containing catalyst contained vanadium in an amount corresponding to 4.0% $V_2O_5$ by weight.

Next, synthesis of phthalic anhydride was carried out by the oxidation of o-xylene using the comparative vanadium-containing catalyst under the same reaction conditions as in Example 1. It was found from the results of analyzing the product that the conversion of o-xylene was 99.9%, the selectivity of phthalic anhydride as the product was 66.9%, and the yield was 66.8%.

It is clear from the results of Example 1 and Comparative Example 1 that the vanadium-containing catalyst of the present invention achieves higher selectivity and yield of phthalic anhydride compared to the conventional vanadium-containing catalyst.

EXAMPLE 2

A proton-type vanadic acid aqueous solution was prepared by passing an ammonium metavanadic acid aqueous solution (concentration=0.1 moles/l) through a column of cation-exchange resin (DOWEX® available from Dow Chemical Company, 50W-X4, 50 to 100 mesh) to perform a cation-exchange. Thereafter, the vanadic acid was left at room temperature for two weeks to spontaneously polycondense. As a result, a dark red polyvanadic acid sol of high viscosity was obtained.

Subsequently, 10.0 g of boehmite powder (specific surface area=320 m$^2$/g) as an inorganic porous substance which was prepared by calcining aluminum hydroxide (special grade, Kanto Chemical Co., Inc.) at 350° C. for six hours, was dispersed in 1 l of water. The temperature was raised to 70° C. with agitation. 88 ml of the polyvanadic acid sol was dropped, and the agitation continued for one hour. As a result, the dark red sol of polyvandic acid faded out and the light yellow slurry was obtained. By filtering the slurry, a colorless transparent filtrate and yellow solid content were obtained. The solid content was dried at 100° C. over one night, and then calcined at 500° C. for three hours to produce a vanadium-containing catalyst. It was found by analyzing the resultant vanadium-containing catalyst in a predetermined method that the catalyst contained vanadium in an amount corresponding to 8.6% $V_2O_5$ by weight. No vanadium was found from the filtrate.

Next, synthesis of isobutene was carried out by the oxidative dehydrogenation of isobutane using the vanadium-containing catalyst. More specifically, first, grains of the vanadium-containing catalyst were arranged into sizes ranging from 9 mesh to 16 mesh. Subsequently, in order to perform a reaction by a fixed-bed flow method, 0.64 g of the vanadium-containing catalyst was diluted with 4 ml of glass beads, and filled in a stainless steel reaction tube with an inner diameter of 10 mm. Thereafter, a mixed gas formed by mixing isobutane, oxygen, and nitrogen in a ratio of 1:0.068:3.3 was arranged to pass through the reaction tube at a rate of 248 ml/min. The reaction was performed under conditions of normal pressures and a temperature of 540° C.

The reaction gas was sampled for 30 minutes after the passage of 30 minutes from the initiation of the reaction, and the product was analyzed using gas chromatography. It was found from the results of analysis that the conversion of isobutane was 7.0%, and the selectivity of isobutene was 63.6%.

Comparative Example 2

A comparative vanadium-containing catalyst was prepared by a known method. More specifically, 50 ml of water was added to 1.03 g of ammonium metavanadate, heated and agitated into slurry. Subsequently, by gradually adding 2.22 g of oxalic acid to the slurry, a homogeneous aqueous solution was obtained. Thereafter, 10 g of the boehmite powder used in Example 2 was added, and agitated at 70° C. for four hours. Thereafter, the aqueous solution was heated to 90° C., and continued to be agitated while evaporating moisture so as to obtain a paste-like composition. The composition was dried at 100° C. over one night, and then calcined at 500° C. for three hours to produce a comparative vanadium-containing catalyst. It was found by analyzing the resultant comparative vanadium-containing catalyst in a predetermined method that the catalyst contained vanadium in an amount corresponding to 8.6% $V_2O_5$ by weight.

Next, synthesis of isobutene was carried out by the oxidative dehydrogenation of isobutane using the comparative vanadium-containing catalyst under the same reaction conditions as in Example 2. It was found from the results of analyzing the product that the conversion of isobutane was 6.9% and the selectivity of isobutene was 54.7%.

It is clear from the results of Example 2 and Comparative Example 2 that the vanadium-containing catalyst of the present invention achieves higher selectivity of isobutene by reactive dehydrogenation of isobutane compared to the conventional vanadium-containing catalyst.

EXAMPLE 3

A vanadium-containing catalyst was prepared in the same manner as in Example 2 except that 10.0 g of the anatase-type titanium dioxide powder used in Example 1 was used instead of the boehmite powder, the amount of polyvanadic acid sol was changed to 26.9 ml, and the final calcination temperature was set at 550° C. The resultant vanadium-containing catalyst contained vanadium in an amount corresponding to 2.4% $V_2O_5$ by weight.

Next, methyl formate was synthesized from methanol using the vanadium-containing catalyst. More specifically, first, grains of the vanadium-containing catalyst were arranged into sizes ranging from 9 mesh to 16 mesh. Subsequently, in order to perform a reaction by a fixed-bed flow method, a stainless steel reaction tube with an inner diameter of 10 mm was filled with 3.0 g of the vanadium-containing catalyst. Thereafter, a mixed gas formed by mixing methanol and air in a mole ratio of 1:5.2 was arranged to pass through the reaction tube at a rate of 75 ml/min. The reaction was performed under conditions of normal pressures and a temperature of 180° C.

After the passage of 30 minutes from the initiation of the reaction, the reaction gas was sampled for 30 minutes, and the product was analyzed using gas chromatography. The results are shown in Table 1.

Comparative Example 3

A comparative vanadium-containing catalyst was prepared in the same manner as in Comparative Example 2 except that 10.0 g of the anatase-type titanium dioxide powder used in Example 1 was used instead of the boehmite powder, the amount of ammonium metavanadate was changed to 0.315 g, the amount of oxalic acid was changed to 0.678 g, and the final calcination temperature was set at 550° C. The resultant comparative vanadium-containing catalyst contained vanadium in an amount corresponding to 2.4% $V_2O_5$ by weight.

Next, methyl formate was synthesized from methanol using the comparative vanadium-containing catalyst under the same conditions as in Example 3. The results are shown in Table 1.

EXAMPLE 4

A vanadium-containing catalyst was prepared in the same manner as in Example 3 except that the amount of polyvanadic acid sol was changed to 45.8 ml, and calcination following to the drying step at 100° C. was not performed. The resultant vanadium-containing catalyst contained vanadium in an amount corresponding to 4.0% $V_2O_5$ by weight.

Next, methyl formate was synthesized from methanol using the vanadium-containing catalyst under the same reaction conditions as in Example 3. The results are shown in Table 1.

Comparative Example 4

A comparative vanadium-containing catalyst was prepared in the same manner as in Comparative Example 3 except that the amount of ammonium metavanadate was changed to 0.536 g, the amount of oxalic acid was changed to 1.55 g, and calcination following to the drying step at 100° C. was not performed. The resultant comparative vanadium-containing catalyst contained vanadium in an amount corresponding to 4.0% of $V_2O_5$ by weight.

Next, methyl formate was synthesized from methanol using the comparative vanadium-containing catalyst under the same reaction conditions as in Example 3. The results are shown in Table 1.

EXAMPLE 5

Titanium hydroxide as an inorganic porous substance was prepared as follows.

181.7 g of an aqueous titanium tetrachloride solution (Ti content=16.5%, Wako Pure Chemical Industries, Ltd.) was slowly dropped into 2 l of water placed in a beaker in an ice-water bath, and agitated. Next, 141 ml of aqueous ammonia (first grade, $NH_3$ content=29%, Kanto Chemical Co., Inc.) was slowly dropped. As a result, gelation proceeded, and white precipitate was generated. A white cake was obtained by filtration. A washing process including adding 2.5 l of water to the cake, agitating the mixture for 30 minutes, and filtering the mixture, was performed. When the cleaning process was repeated five times, $Cl^-$ ions were not detected from the filtrate, and therefore washing was stopped. The resultant cake was dried at 110° C. over one night, and 52.5 g of titanium hydroxide was obtained. According to the results of an X-ray fluorescence analysis of the titanium hydroxide, the titanium hydroxide contained 48.9% Ti by weight which was equivalent to 42.8 g of $TiO_2$. The titanium hydroxide was pulverized with a ball mill so as to produce powders of a size not larger than 100 mesh. The specific surface area of the titanium hydroxide powder was 376 $m^2/g$.

A vanadium-containing catalyst was prepared in the same manner as in Example 2 except that 10.0 g of the titanium hydroxide was used instead of the boehmite powder, the amount of polyvanadic acid sol was changed to 38.2 ml, and the final calcination temperature was set at 600° C. The resultant vanadium-containing catalyst contained vanadium in an amount corresponding to 4.1% $V_2O_5$ by weight.

Next, methyl formate was synthesized from methanol using the vanadium-containing catalyst under the same reaction conditions as in Example 3 except that the reaction temperature and gas flow rate were changed to 170° C. and 56 ml/min, respectively. The results are shown in Table 1.

Comparative Example 5

As an inorganic porous substance, the titanium hydroxide powder prepared in Example 5 was used. A comparative vanadium-containing catalyst was prepared in the same manner as in Comparative Example 2 except that 10.0 g of the titanium hydroxide was used instead of the boehmite powder, the amount of ammonium metavanadate was changed to 0.447 g, the amount of oxalic acid was changed to 0.963 g, and the calcination temperature was set at 600° C. The resultant comparative vanadium-containing catalyst contained vanadium in an amount corresponding to 4.1% of $V_2O_5$ by weight.

Next, methyl formate was synthesized from methanol using the comparative vanadium-containing catalyst under the same reaction conditions as in Example 5. The results are shown in Table 1.

EXAMPLE 6

Zirconium hydroxide as an inorganic porous substance was prepared as follows.

100.0 g of zirconyl nitrate (special grade, Mitsuwa Chemical Industries, Ltd.) was added to 2.5 l of water, and dissolved by agitation. Next, 58 ml of aqueous ammonia (first grade, $NH_3$ content=29%, Kanto Chemical Co., Inc.) was slowly dropped. As a result, gelation proceeded, and white precipitate was generated. A white cake was obtained by filtration. A cleaning process including adding 2.5 l of water to the cake, agitating the mixture for 30 minutes, and filtering, was performed. After repeating the washing process five times, the washing process was stopped. The resultant cake was dried at 110° C. over one night, and 42.8 g of zirconium hydroxide was obtained. According to the results of an X-ray fluorescence analysis of the zirconium hydroxide, the zirconium hydroxide contained 57.3% Zr by weight which was equivalent to 33.1 g of $ZrO_2$. The zirconium hydroxide was pulverized with a ball mill so as to produce powders of a size not larger than 100 mesh. The specific surface area of the zirconium hydroxide powder was 275 $m^2/g$.

A vanadium-containing catalyst was prepared in the same manner as in Example 2 except that 10.0 g of the zirconium hydroxide was used instead of the boehmite powder, and the amount of polyvanadic acid sol was changed to 67.2 ml. The resultant vanadium-containing catalyst contained vanadium in an amount corresponding to 7.4% $V_2O_5$ by weight.

Next, methyl formate was synthesized from methanol using the vanadium-containing catalyst under the same reaction conditions as in Example 3 except that the reaction temperature was set at 170° C. The results are shown in Table 1.

Comparative Example 6

As an inorganic porous substance, the zirconium hydroxide powder prepared in Example 6 was used. A comparative vanadium-containing catalyst was prepared in the same manner as in Comparative Example 2 except that 10.0 g of the zirconium hydroxide powder was used instead of the boehmite powder, the amount of ammonium metavanadate was changed to 0.786 g, and the amount of oxalic acid was changed to 1.695 g. The resultant comparative vanadium-containing catalyst contained vanadium in an amount corresponding to 7.4% of $V_2O_5$ by weight.

Next, methyl formate was synthesized from methanol using the comparative vanadium-containing catalyst under the same reaction conditions as in Example 6. The results are shown in Table 1.

EXAMPLE 7

A vanadium-containing catalyst was prepared in the same manner as in Example 2 except that 10.0 g of niobic acid powder ($Nb_2O_5$ content=80.4%, the specific surface area= 166 $m^2/g$, available from C.B.M.M.) was used instead of the boehmite powder, and the amount of polyvanadic acid sol was changed to 39.9 ml. The resultant vanadium-containing catalyst contained 4.3% $V_1O_4$ by weight.

Next, methyl formate was synthesized from methanol using the vanadium-containing catalyst under the same reaction conditions as in Example 3. The results are shown in Table 1.

Comparative Example 7

A comparative vanadium-containing catalyst was prepared in the same manner as in Comparative Example 2 except that 10.0 g of the niobic acid powder used in Example 7 was used instead of the boehmite powder, the amount of ammonium metavanadate was changed to 0.467 g, and the amount of oxalic acid was changed to 1.006 g. The resultant comparative vanadium-containing catalyst contained vanadium in an amount corresponding to 4.3% of $V_2O_5$ by weight.

Next, methyl formate was synthesized from methanol using the comparative vanadium-containing catalyst under the same reaction conditions as in Example 3. The results are shown in Table 1.

TABLE 1

| | Inorganic porous substance | Gas conditions | Reaction temp. (° C.) | Conversion of methanol | Selectivity (%) Methyl formate | form-aldehyde | Methyl formate | Yield (%) Methyl formate + form-aldehyde |
|---|---|---|---|---|---|---|---|---|
| Example 3 | Titanium dioxide | A | 180 | 91.9 | 50.5 | 20.8 | 47.3 | 66.4 |
| Comparative Example 3 | Titanium dioxide | A | 180 | 65.3 | 33.2 | 36.8 | 21.7 | 45.7 |

TABLE 1-continued

|  | Inorganic porous substance | Gas conditions | Reaction temp. (° C.) | Conversion of methanol | Selectivity (%) | | Yield (%) | |
|---|---|---|---|---|---|---|---|---|
|  |  |  |  |  | Methyl formate | formaldehyde | Methyl formate | Methyl formate + formaldehyde |
| Example 4 | Titanium dioxide | A | 180 | 88.0 | 33.4 | 43.0 | 29.4 | 67.2 |
| Comparative Example 4 | Titanium dioxide | A | 180 | 29.9 | 13.5 | 30.6 | 4.0 | 13.1 |
| Example 5 | Titanium hydroxide | B | 170 | 87.9 | 65.6 | 6.7 | 57.7 | 63.6 |
| Comparative Example 5 | Titanium hydroxide | B | 170 | 67.0 | 46.2 | 20.9 | 31.0 | 45.0 |
| Example 6 | Zirconium hydroxide | A | 170 | 74.6 | 73.9 | 9.3 | 55.2 | 62.2 |
| Comparative Example 6 | Zirconium hydroxide | A | 170 | 68.5 | 59.0 | 9.6 | 40.4 | 47.0 |
| Example 7 | Niobic acid | A | 180 | 86.9 | 57.2 | 22.0 | 49.7 | 68.8 |
| Comparative Example 7 | Niobic acid | A | 180 | 85.6 | 50.1 | 24.2 | 42.9 | 63.6 |

Gas conditions A: methanol/air = 1/5.2 (mole ratio), 75 ml/min.
Gas conditions B: methanol/air = 1/5.2 (mole ratio), 56 ml/min.

It was understood from the results of Examples 3 to 7 and Comparative Examples 3 to 7 that the vanadium-containing catalysts of the present invention achieve higher activity and selectivity in the synthesis of methyl formate from methanol compared to the conventional vanadium-containing catalysts.

EXAMPLE 8

A vanadium-containing catalyst was prepared in the same manner as in Example 3 except that the final calcination temperature was set at 500° C. The resultant vanadium-containing catalyst contained vanadium in an amount corresponding to 2.4% $V_2O_5$ by weight.

Next, benzaldehyde and benzoic acid were synthesized by the oxidation of toluene using the vanadium-containing catalyst. More specifically, the grains of the vanadium-containing catalyst were arranged into sizes ranging from 9 mesh to 16 mesh. Subsequently, in order to perform a reaction by a fixed-bed flow method, a stainless steel reaction tube with an inner diameter of 10 mm was filled with 0.77 g of the vanadium-containing catalyst diluted with 4 ml of glass beads. Thereafter, air containing 0.9% toluene was arranged to pass through the reaction tube at a rate of 533 ml/min. The reaction was performed under conditions of normal pressures and a temperature of 320° C.

After the passage of 30 minutes from the initiation of the reaction, the reaction gas was sampled for 30 minutes, and the product was analyzed using gas chromatography. According to the results, the conversion of toluene was 16.1%, the selectivity of benzaldehyde was 22.9%, and the selectivity of benzoic acid was 30.1%.

Comparative Example 8

A comparative vanadium-containing catalyst was prepared in the same manner as in Comparative Example 3 except that the final calcination temperature was set at 500° C. The resultant comparative vanadium-containing catalyst contained 2.4% $V_2O_5$ by weight.

Next, benzaldehyde and benzoic acid were synthesized by the oxidation of toluene using the comparative vanadium-containing catalyst under the same reaction conditions as in Example 8. According to the results, the conversion of toluene was 10.9%, the selectivity of benzaldehyde was 19.4%, and the selectivity of benzoic acid was 25.4%.

As is clear from the results of Example 8 and Comparative Example 8, the vanadium-containing catalyst of the present invention achieves higher activity and selectivity compared to the conventional vanadium-containing catalyst in both the synthesis of benzaldehyde and the synthesis of benzoic acid by the oxidation of toluene.

EXAMPLE 9

6.0 g of diatomaceous earth "Celite" (available from Johns-Manville Product, the specific surface area=28 $m^2/g$) as an inorganic porous substance was added to 50 ml of polyvanadic acid sol (0.1 moles/l) which is the same as that used in Example 2, and agitated at 70° C. for 30 minutes. Subsequently, 1.73 g of phosphoric acid (as a reagent of Kanto Chemical Co., Inc., special grade, concentration of $H_3PO_4$=85%) was added, and agitated for 30 minutes. Furthermore, an aqueous solution formed by dissolving 3.90 g of cesium nitrate (purity=99.9%, Wako Pure Chemical Industries, Ltd.) and 0.85 g of silver nitrate (as a reagent of Wako Pure Chemical Industries, Ltd., special grade) in 50 ml of water was added. Agitation was performed for two hours while keeping the temperature of the mixture at 70° C. Thereafter, the mixture was heated to 90° C., and continued to be agitated while evaporating moisture so as to obtain a paste-like composition. The composition was dried at 120° C. over 14 hours, calcined at 230° C. for four hours, and further calcined at 600° C. for three hours to produce a vanadium containing catalyst. The resultant vanadium-containing catalyst contained vanadium in an amount corresponding to 30.3% $V_2O_5$ by weight. The mole ratio of V:P:Cs:Ag was 1:0.3:0.4:0.1.

Next, anisaldehyde was synthesized by the oxidation of p-methoxy toluene (p-methyl anisole) using the vanadium-containing catalyst. More specifically, first, grains of the vanadium-containing catalyst were arranged into sizes ranging from 9 mesh to 16 mesh. Subsequently, in order to perform a reaction by a fixed-bed flow method, a stainless steel reaction tube with an inner diameter of 10 mm was filled with 5.0 g of the vanadium-containing catalyst. Thereafcter, air containing 1% p-methoxy toluene was arranged to pass through the reaction tube at a rate of 350 ml/min. The reaction was performed under conditions of normal pressures and a temperature of 420° C.

After the passage of 30 minutes from the initiation of the reaction, the reaction gas was sampled for 30 minutes, and the product was analyzed using gas chromatography. According to the results, the conversion of p-methoxy toluene was 95.2%, and the selectivity of anisaldehyde was 86.5%

Comparative Example 9

5.85 g of ammonium metavanadate was dissolved in 500 ml of water. The mixture was heated to 70° C., and agitated. Subsequently, 1.73 g of 85% phosphoric acid was added. Furthermore, an aqueous solution formed by dissolving 3.90 g of cesium nitrate and 0.85 g of silver nitrate in 50 ml of water was added, and agitated for one hour while keeping the temperature of the mixture at 70° C. Next, 6.0 g of diatomaceous earth "Celite" which is the same as that used in Example 9 was added, and agitated for two hours while keeping the temperature at 70° C. Then, the mixture was heated to 90° C., and continued to be agitated while evaporating moisture so as to obtain a paste-like composition. The composition was dried at 120° C. over 14 hours, calcined at 230° C. for four hours, and further calcined at 600° C. for three hours to produce a comparative vanadium containing catalyst. The resultant comparative vanadium-containing catalyst contained vanadium in an amount corresponding to 30.3% $V_2O_5$ by weight. The mole ratio of V:P:Cs:Ag was 1:0.3:0.4:0.1.

Next, anisaldehyde was synthesized by the oxidation of p-methoxy toluene using the comparative vanadium-containing catalyst under the same reaction conditions as in Example 9. According to the results, the conversion of p-methoxy toluene was 94.8%, and the selectivity of anisaldehyde was 80.1%.

It is clear from the results of Example 9 and Comparative Example 9 that the vanadium-containing catalyst of the present invention achieves higher selectivity compared to the conventional vanadium-containing catalyst in the synthesis of anisaldehyde by the oxidation of p-methoxy toluene.

EXAMPLE 10

Magnesium oxide as an inorganic porous substance to be used as a starting material was prepared as follows. 97.7 g of magnesium nitrate hexahydrate (a reagent of Kanto Chemical Co., Inc., special grade) was dissolved in 300 ml of water. Then, ammonium carbonate (a reagent of Kanto Chemical Co., Inc., special grade) was added until the pH of the liquid reached seven. After filtration, a five-minute agitation washing process using 250 ml of water was repeated four times. The resultant white cake was dried over 120° C. over 14 hours and calcined at 700° C. for three hours, and then pulverized with a ball mill to obtain magnesium oxide powder. The specific surface area of the magnesium oxide powder was 59 $m^2/g$.

130 ml of water was added to 174 ml of the same polyvanadic acid sol as that used in Example 2, and then the temperature was raised to 70° C. with agitation. 3.0 g of the magnesium oxide powder was added while agitating the mixture. After agitating the resultant mixture for two hours, the mixture was heated to 90° C., and then condensed by heating and agitation for six hours. The resultant paste was dried at 120° C. for 14 hours, and calcined at 550° C. for six hours so as to obtain a vanadium-containing catalyst. The resultant vanadium-containing catalyst contained vanadium in an amount corresponding to 24.0% $V_2O_5$ by weight.

Next, synthesis of propylene was carried out by the oxidative dehydrogenation of propane using the vanadium-containing catalyst. More specifically, first, grains of the vanadium-containing catalyst were arranged into sizes ranging from 9 mesh to 16 mesh. Subsequently, in order to perform a reaction by a fixed-bed flow method, 0.60 g of the vanadium-containing catalyst was diluted with 4 ml of glass beads, and filled in a stainless steel reaction tube with an inner diameter of 10 mm. Thereafter, air containing 2% propane was arranged to pass through the reaction tube at a rate of 100 ml/min. The reaction was performed under conditions of normal pressures and a temperature of 510° C.

After the passage of 30 minutes from the initiation of the reaction, the reaction gas was sampled for 30 minutes, and the product was analyzed using gas chromatography. It was found from the results of analysis that the conversion of propane was 25.5%, and the selectivity of propylene as the product was 41.3%.

Comparative Example 10

300 ml of water was added to 2.033 g of ammonium metavanadate, and then the temperature was raised to 70° C. with agitation. Subsequently, 5.0 g of the magnesium oxide powder prepared in Example 10 was added, and agitated for two hours. The resultant mixture underwent the same processes as in Example 10 to prepare a comparative vanadium-containing catalyst. The resultant vanadium-containing catalyst contained vanadium in an amount corresponding to 24.0% $V_2O_5$ by weight.

Next, synthesis of propylene was carried out by the oxidative dehydrogenation of propane using the comparative vanadium-containing catalyst under the same reaction conditions as in Example 10. According to the results, the conversion of propane was 25.7%, and the selectivity of propylene was 32.7%.

It is clear from the results of Example 10 and Comparative Example 10 that the vanadium-containing catalyst of the present invention achieves higher selectivity when synthesizing propylene by the oxidative dehydrogenation of propane compared to the conventional vanadium-containing catalyst.

EXAMPLE 11

152.4 g of alumina sol (product name "A-200", available from Nissan Chemical Industries, Ltd., concentration of $Al_2O_3$=10.5%) as a precursor of an inorganic porous substance, 19.5 g of silica sol (product name "Snowtex O", available from Nissan Chemical Industries, Ltd., concentration of $SiO_2$=20.5%), and 120 ml of water were placed in a flask provided with an agitator and a cooling tube. Heating and agitation (mixing) were performed at 80° C. A suspension was formed by adding 300 ml of water to 18.14 g of antimony trioxide powder (a reagent of Kishida Chemistry Co. Ltd., special grade, purity of $Sb_2O_3$=98%) . Subsequently, 73.2 g of tartaric acid was added to the suspension, heated and dissolved therein so as to form a homogeneous solution. The resultant homogeneous solution was added to the above-mentioned mixture. Furthermore, 244 ml of the same polyvanadic acid sol (the concentration= 0.1 moles/l) as that used in Example 2 was added, and heated to 90° C. so as to perform heating reflux over 17 hours. Thereafter, the solution was placed in a beaker, and condensed by performing heating and agitation at 90° C. for six hours to evaporate moisture. The resultant paste was dried at 120° C. four for 14 hours, calcined at 230° C. for four hours, and further calcined at 550° C. for three hours to obtain a vanadium-containing catalyst. The resultant vanadium-containing catalyst contained vanadium in an amount corresponding to 5.5% $V_2O_5$ by weight. The mole ratio of V:Sb was 1:5.

Next, ammoxidation of propane was carried out using the vanadium-containing catalyst. More specifically, first, grains of the vanadium-containing catalyst were arranged into sizes ranging from 9 mesh to 16 mesh. Subsequently, in order to perform a reaction by a fixed-bed flow method, 4.0 g of the vanadium-containing catalyst was filled in a stainless steel reaction tube with an inner diameter of 10 mm. Thereafter, a mixed gas formed by $C_3H_8$, $NH_3$, $O_2$, $N_2$, $H_2O$ in a mole ratio of 1:2:4:7.5:4 was arranged to pass through the reaction tube at a rate of 75 ml/min. The reaction was performed under conditions of normal pressures and a temperature of 500° C.

After the passage of 30 minutes from the initiation of the reaction, the reaction gas was sampled for 30 minutes, and the product was analyzed using gas chromatography. It was found from the results of analysis that the conversion of propane was 63.2%, the selectivity of acrylonitrile as the product was 40.1%, the selectivity of propylene was 11.4%, and the selectivity of HCN was 10.5%.

Comparative Example 11

200 ml of water was added to 2.86 g of ammonium metavanadate, heated and agitated into slurry. 6.15 g of oxalic acid was added to the slurry and dissolved therein to form a homogeneous solution. A comparative vanadium-containing catalyst was prepared in the same manner as in Example 11 except that the homogeneous solution was used instead of the polyvanadic acid sol. The vanadium-containing catalyst contained vanadium in an amount corresponding to 5.5% $V_2O_5$ by weight. The mole ratio of V:Sb was 1:5.

Next, ammoxidation of propane was carried out using the comparative vanadium-containing catalyst under the same reaction conditions as in Example 11. According to the results, the conversion of propane was 56.1%, the selectivity of acrylonitrile was 35.9%, the selectivity of propylene was 10.1%, and the selectivity of HCN was 10.4%.

It is clear from results of Example 11 and Comparative Example 11 that the vanadium-containing catalyst of the present invention achieves higher selectivity compared to the conventional vanadium-containing catalyst in the synthesis of acrylonitrile by the ammoxidation of propane.

While the invention has been described with reference to the examples and comparative examples presented in the BEST MODE FOR IMPLEMENTING THE INVENTION section, it is not intended that this description be construed in a limiting sense. The invention may be varied in many ways, and such variations are not to be regarded as a departure from the spirit and scope of the invention and are intended to be included within the scope of the claims.

Indutrial Applicability

As described above, the vanadium-containing catalysts of the present invention are obtained by using polyvanadic acids as a source of vanadium. Moreover, as discussed above, the vanadium-containing catalysts of the present invention are formed by mixing catalyst components other than vanadium, or their precursors, with a polyvanadic acid sol formed by ion-exchanging a metavanadic acid aqueous solution with a proton-type cation-exchange resin and performing polycondensation, and then drying and/or calcining the mixture.

Compared to the conventional vanadium-containing catalysts, the vanadium-containing catalysts of the present invention achieve higher catalytic activity, and have longer life. Additionally, the vanadium-containing catalysts of the present invention achieve excellent dispersion and thermal stability, and do not deteriorate even when used at high temperatures. Thus, the vanadium-containing catalysts can fully exhibit their catalytic activity under mild reaction conditions, and can be suitably used for various reactions including oxidation reactions of aromatic hydrocarbon, heterocyclic compound, saturated aliphatic hydrocarbon, unsaturated aliphatic hydrocarbon, and derivatives thereof, for example, various partial oxidation reactions, such as synthesis of phthalic anhydride from o-xylene or naphthalene, synthesis of pyromellitic dianhydride from durene, synthesis of maleic anhydride from benzene or n-butane, synthesis of (substituted) benzaldehyde from (substituted) toluene, synthesis of benzoic acid from toluene, synthesis of pyridine carboxylic acids by the oxidation of picoline, lutidine, quinoline, etc., synthesis of formaldehyde from methane, and synthesis of (meth)acrylic acid from (meth)acrolein; various oxidative dehydrogenation reactions, such as synthesis of propylene and butenes by the oxidative dehydrogenation of propane and butanes, and synthesis of formaldehyde and methyl formate from methanol; various ammoxydation reactions, such as synthesis of benzonitrile by the ammoxydation of toluene, and synthesis of acrylonitrile and methacrylonitrile by the ammoxydation of propane and isobutane; oxidation reactions of inorganic compounds, such as synthesis of sulfuric acid by the oxidation of $SO_2$; reductive denitration of nitrogen oxide by means of ammonia; decomposition reactions of organic halides; hydrogenation reactions; dehydrogenation reactions; hydrodesulfurization reactions; isomerization reactions; alkylation reactions; dehydration reactions; polymerization reactions: and photocatalytic reactions.

As described above, the process for manufacturing a vanadium-containing catalyst of the present invention includes the steps of mixing polyvanadic acid with catalyst components other than vanadium or their precursors, and drying and/or calcining the mixture. This process allows the manufacture of vanadium-containing catalysts which achieve higher catalytic activity, longer life, excellent dispersion and thermal stability compared to conventional vanadium-containing catalysts, and do not deteriorate even when used at high temperatures. Thus, the vanadium-containing catalysts according to the present invention can fully exhibit their catalytic activity under mild reaction conditions, and can be suitably used for various reactions mentioned above.

As described above, the process for manufacturing phthalic anhydride of the present invention is a process of contacting a mixed gas containing o-xylene and molecular oxygen with a vanadium-containing catalyst which is obtained by using polyvanadic acid as a source of vanadium. This process allows an efficient manufacture of phthalic anhydride.

As described above, a process, for manufacturing isobutene of the present invention is a process of contacting a mixed gas containing isobutane and molecular oxygen with a vanadium-containing catalyst which is obtained by using polyvanadic acid as a source of vanadium. This process allows an efficient manufacture of isobutene.

As described above, a process for manufacturing methyl formate of the present invention is a process of contacting a mixed gas containing methanol and molecular oxygen with a vanadium-containing catalyst which is obtained by using polyvanadic acid as a source of vanadium. This process allows an efficient manufacture of methyl formate.

As described above, a process for manufacturing benzaldehyde of the present invention is a process of contacting a mixed gas containing toluene and molecular oxygen with a vanadium-containing catalyst which is obtained by using polyvanadic acid as a source of vanadium. This process allows an efficient manufacture of benzaldehyde.

As described above, a process for manufacturing benzoic acid of the present invention is a process of contacting a mixed gas containing toluene and molecular oxygen with a vanadium-containing catalyst which is obtained by using polyvanadic acid as a source of vanadium. This process allows an efficient manufacture of benzoic acid.

As described above, a process for manufacturing anisaldehyde of the present invention is a process of contacting a mixed gas containing p-methoxy toluene and molecular oxygen with a vanadium-containing catalyst which is obtained by using polyvanadic acid as a source of vanadium. This process allows an efficient manufacture of anisaldehyde.

As described above, a process for manufacturing propylene of the present invention is a process of contacting a mixed gas containing propane and molecular oxygen with a vanadium-containing catalyst which is obtained by using polyvanadic acid as a source of vanadium. This process allows an efficient manufacture of propylene.

As described above, a process for manufacturing acrylonitrile of the present invention is a process of contacting a mixed gas containing propane, molecular oxygen, and ammonia with a vanadium-containing catalyst which is obtained by using polyvanadic acid as a source of vanadium. This process allows an efficient manufacture of acrylonitrile.

What is claimed is:

1. A process for manufacturing isobutene by contacting a mixed gas containing isobutane and molecular oxygen with a vanadium-containing catalyst which is obtained by using a polyvanadic acid as a source of vanadium.

2. A process for manufacturing methyl formate by contacting a mixed gas containing methanol and molecular oxygen with a vanadium-containing catalyst which is obtained by using a polyvanadic acid as a source of vanadium.

3. A process for manufacturing propylene by contacting a mixed gas containing propane and molecular oxygen with a vanadium-containing catalyst which is obtained by using a polyvanadic acid as a source of vanadium.

4. A process for manufacturing acrylonitrile by contacting a mixed gas containing propane, molecular oxygen and ammonia with a vanadium-containing catalyst which is obtained by using a polyvanadic acid as a source of vanadium.

5. A method of performing partial oxidation of a heterocyclic hydrocarbon comprising contacting a mixed gas containing a heterocyclic hydrocarbon and molecular oxygen with a vanadium-containing catalyst obtained using a polyvanadic acid as a source of vanadium.

6. A method of partial oxidation of a saturated aliphatic hydrocarbon comprising contacting a mixed gas containing a saturated aliphatic hydrocarbon and molecular oxygen with a vanadium-containing catalyst obtained using a polyvanadic acid as a source of vanadium.

7. A method of partial oxidation of an aldehyde comprising contacting a mixed gas containing an aldehyde and molecular oxygen with a vanadium-containing catalyst obtained using a polyvanadic acid as a source of vanadium.

8. A method of oxidative dehydrogenation of an organic substance comprising contacting a mixed gas containing an organic substance and molecular oxygen with a vanadium-containing catalyst obtained using a polyvanadic acid as a source of vanadium.

9. The method of oxidative dehydrogenation of an organic substance of claim 8, wherein said organic substance is a saturated aliphatic hydrocarbon.

10. The method of oxidative dehydrogenation of an organic substance of claim 9, wherein said saturated aliphatic hydrocarbon is propane.

11. The method of oxidative dehydrogenation of an organic substance of claim 9, wherein said saturated aliphatic hydrocarbon is isobutane.

12. The method of oxidative dehydrogenation of an organic substance of claim 8, wherein said organic substance is an alcohol.

13. The method of oxidative dehydrogenation of an organic substance of claim 12, wherein said alcohol is methanol.

14. A method of performing ammoxidation of an organic substance comprising contacting a mixed gas containing an organic substance, molecular oxygen and ammonia with a vanadium-containing catalyst obtained using a polyvanadic acid as a source of vanadium.

15. The method of performing ammoxidation of an organic substance of claim 14, wherein said organic substance is an aromatic hydrocarbon.

16. The method of performing ammoxidation of an organic substance of claim 14, wherein said organic substance is a saturated aliphatic hydrocarbon.

17. The method of performing ammoxidation of an organic substance of claim 16, wherein said saturated aliphatic hydrocarbon is propane.

18. A method of performing an oxidation reaction of sulfur dioxide comprising contacting a mixed gas containing sulfur dioxide and molecular oxygen with a vanadium-containing catalyst obtained using a polyvanadic acid as a source of vanadium.

19. A method of performing a decomposition reaction of an organic halide comprising contacting an organic halide with a vanadium-containing catalyst obtained using a polyvanadic acid as a source of vanadium.

* * * * *

UNITED STATES PATENT AND TRADEMARK OFFICE
CERTIFICATE OF CORRECTION

PATENT NO.    : 6,281,378 B1
DATED         : August 28, 2001
INVENTOR(S)   : Nobuji Kishimoto et al.

It is certified that error appears in the above-identified patent and that said Letters Patent is hereby corrected as shown below:

<u>Title page,</u>
Item [62], Related U.S. Application Data, "Division of application No. 09/109,147, filed on Nov. 12, 1998" should be -- Division of application No. 09/190,147, filed on Nov. 12, 1998 --.

Signed and Sealed this

Fourteenth Day of May, 2002

*Attest:*

JAMES E. ROGAN
*Attesting Officer*            *Director of the United States Patent and Trademark Office*